United States Patent [19]

Sumikawa et al.

[11] 4,035,419
[45] July 12, 1977

[54] PROCESS FOR THE PREPARATION OF MALIC ACID CRYSTALS

[76] Inventors: Shozo Sumikawa, 2-9, Kyowa-cho, Hofu; Shinichiro Sakaguchi, 2212-34, Ikuma-cho; Tomoo Okiura, 2273, Ikuwa-cho, both of Yokkaichi, all of Japan

[21] Appl. No.: 658,296

[22] Filed: Feb. 17, 1976

[51] Int. Cl.² .................................... C07C 59/12
[52] U.S. Cl. .................... 260/535 P; 260/537 N
[58] Field of Search .............................. 260/535 P

[56] References Cited

U.S. PATENT DOCUMENTS 3,875,222   4/1975   Weinrotter et al. ............ 260/535 P Primary Examiner—Paul J. Killos
Attorney, Agent, or Firm—Glenn K. Robbins

[57] ABSTRACT

A process for producing crystals of malic acid having a uniform high purity using maleic acid or fumaric separately or together. The reaction mixture is cooled, resulting solids are separated and the resulting liquid is concentrated and then cooled to a specified temperature range according to the concentration of malic acid in weight %. The resulting solid is separated and the remaining liquid is cooled to 19° to 21° C to crystallize malic acid.

1 Claim, 2 Drawing Figures

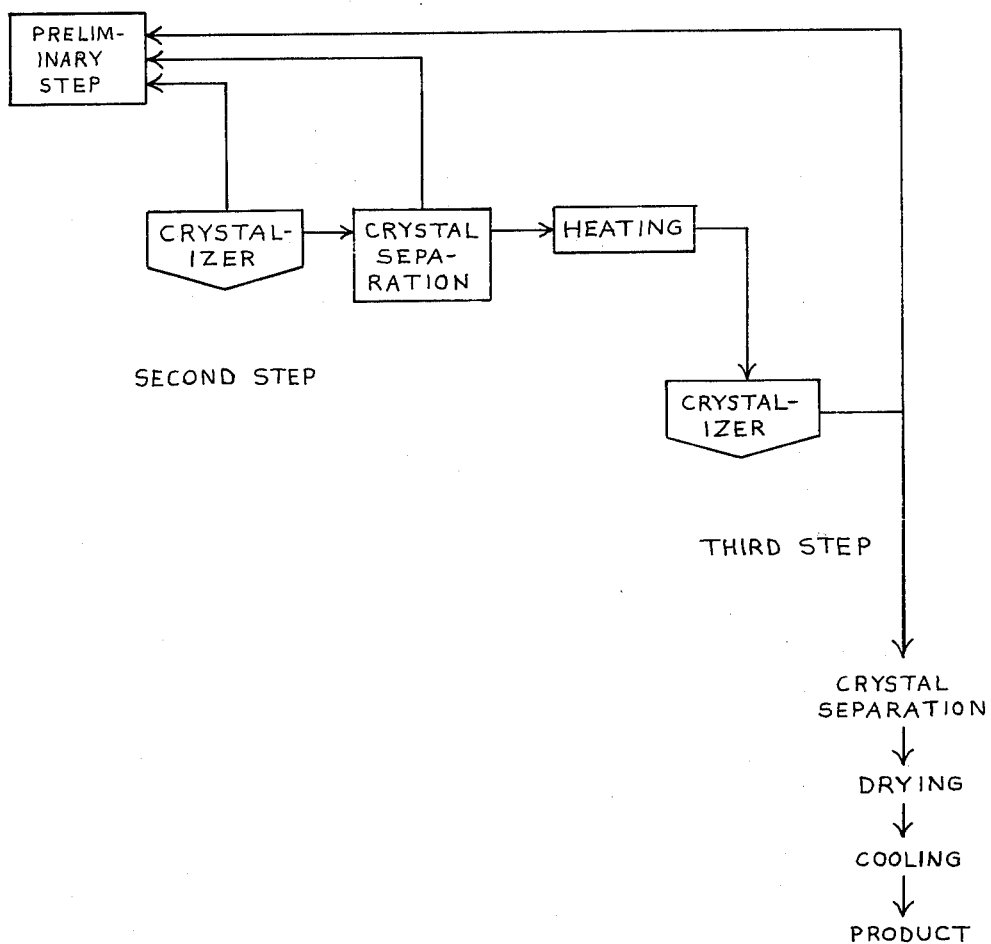

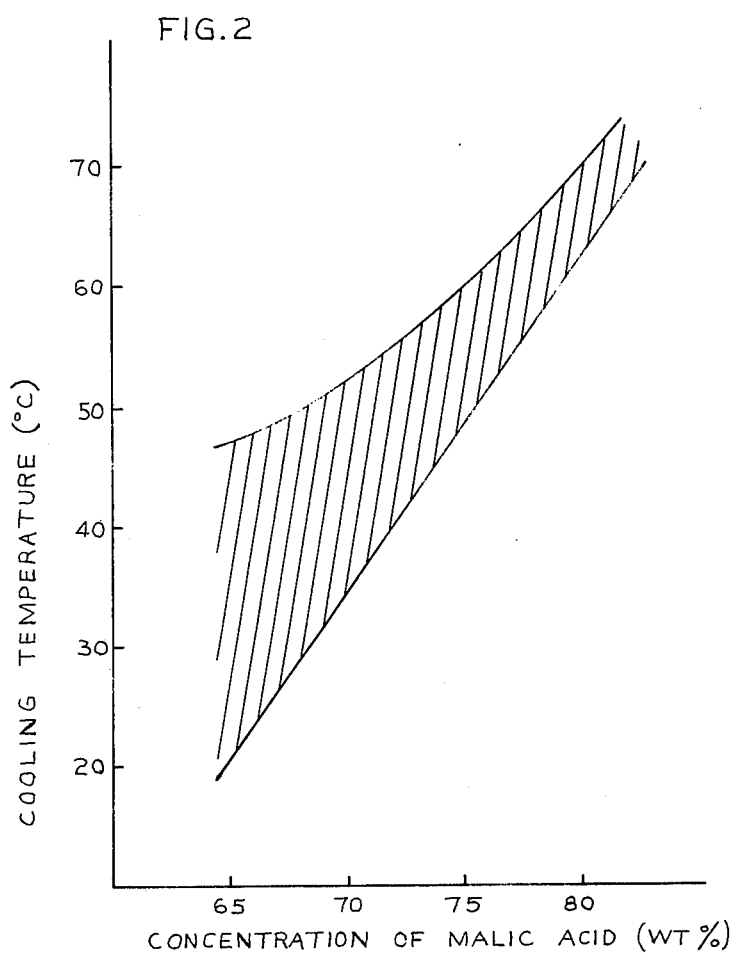

PROCESS FOR THE PREPARATION OF MALIC ACID CRYSTALS

BACKGROUND OF THE INVENTION

This invention relates to an improvement for producing crystals of malic acid having a uniform high purity in the production of malic acid by using maleic acid and/or fumaric acid as a raw material. Malic acid is in great demand as food-additives such as flavoring agent, acid-tasting agent, etc. Therefore, it is required to produce malic acid crystals of a uniform high purity.

The production of malic acid (in a D,L form) by heating an aqueous solution of maleic acid and/or fumaric acid is well known.

In the known process, maleic acid and/or fumaric acid is dissolved in water in an amount of 30–130 g per 100 ml of water. The solution is heated in an autoclave at 150°–250° C for about 3–10 hours to form malic acid. The resulting reaction mixture contains trace to about 3% of maleic acid, about 30–70% of fumaric acid and about 30–70% of the desired malic acid (percentages are based on the total amount of acids). As the first step for isolating malic acid from the reaction mixture, the mixture is cooled at 10°–40° C, usually 20°–30° C to precipitate and remove fumaric acid having a low solubility. The resulting mother liquor still contains 1–3%, usually about 1.6% of fumaric acid. It is obviously disadvantageous to further cool the mother liquor to remove the remaining fumaric acid, since a large amount of malic acid is precipitated together with fumaric acid in such a cooling. Accordingly, there has been no choice in a conventional process for the isolation of malic acid but to directly subject the mother liquor to decolorization and concentration followed by the crystallization of malic acid. Sometimes, the unreacted maleic acid is removed from the mother liquor prior to the concentration of the mother liquor, but usually the maleic acid is retained in the mother liquor under properly controlled conditions while malic acid is crystallized in and isolated from the mother liquor. The isolated crystals of malic acid are dried for finishing.

The crystallization of malic acid is effected by cooling the concentrated mother liquor containing malic acid usually in a ratio of 65–80% based on the total amount of the acids. However, according to the conventional process, it is very difficult to stabilize the formation of malic acid crystals of a high purity and proper size. When, for example, the concentrated mother liquor obtained after separating fumaric acid crystals from the reaction mixture, is left to stand for about 5 hours and then cooled with water for about 20 hours, the concentrate is converted to a paste. It is difficult to isolate malic acid crystals from the paste. Malic acid crystals separated from the paste not only have a low purity but also are irregular in size. Among the crystals there are contained crystals of a microscopic size.

The present inventors have made various studies on the isolation of crystals of a desired compound from such an aqueous solution of organic acids as the above-mentioned concentrate, from which it has been difficult to separate the crystals favorable in properties. As the result, it has been found that crystals having a high purity are readily obtained by: as the second step, cooling the aqueous solution of organic acids as mentioned above (for a specific example, the aforementioned aqueous solution of malic acid obtained after the first step of the separation of fumaric acid and the concentration of the mother liquor) at a temperature within a given range in order to effect the crystallization of the remaining fumaric acid, and separating the resulting crystals with a comparatively small loss of malic acid; and, as the third step, cooling the resulting residue to effect the crystallization of malic acid and separating the resulting malic acid crystals. The present invention has been accomplished on the basis of this finding.

Particularly, it has been found that malic acid crystals, which are uniform and filtered off, are produced by cooling as the second step the aqueous solution of malic acid having such a high concentration as 55–90%, usually 65–80% obtained in accordance with the aforementioned manner, at 21°–70° C, exactly, at a temperature within the range shown as a shade in FIG. 2; and cooling as the third step the filtrate obtained after separating the resulting crystals in order to crystallize malic acid. In FIG. 2, the cooling in the shaded area can be expressed as cooling the concentrate having a concentration of 65–80% by weight at a temperature of about 20°–45° C at the lower weight percent and about 65°–75° C at the higher weight percent. The cooling at intermediate concentrations is carried out generally on a straight line basis between the lower temperature ranges and slightly under the upper temperature ranges on a straight basis.

OBJECTS AND DRAWING

The above features are objects of this invention. Further objects will appear in the detailed description below and will be otherwise apparent to those skilled in the art.

For the purpose of illustration of this invention an example is shown in the drawings below. It is to be understood that these drawings are for the purpose of illustration only and that the invention is not limited thereto.

IN THE DRAWINGS

FIG. 1, is a flow diagram of the process of the present invention.

FIG. 2, shows the relation between the malic acid concentration in the feed solution for crystallization and the cooling temperature in the first step.

DESCRIPTION OF THE INVENTION:

The aqueous solution of malic acid having such a high concentration as 55–90%, usually 65–80% is, as is shown in FIG. 1, cooled in the second step at 21–70° C, exactly, at a temperature within the range shown as a shade in FIG. 2. The resulting crystals are separated. Usually, filtration is advantageous to separate the crystals, but any other conventional separation methods than filtration may be used for the separation.

As a result of this separation, the concentration of fumaric acid is remarkably lowered. In any case in the present process, regardless of the conditions in the first step, the concentration of fumaric acid after this separation is 1.0% or less based on the total amount of the acids. The decrease of the concentration of malic acid is very slight. From the foregoing, the effect brought about by the second step is considered much more significant as compared with that brought about by the first step. When there are contained microscopic crystals in the filtrate obtained in the second step, the filtrate is heated to dissolve the crystals and then passed to the third step. In the third step, the aqueous solution containing 1.0% or less of fumaric acid and a large amount, usually 65–80%, of malic acid is cooled. At a proper time, seed crystals are added to the solution. The crystallization is effected at 19°–21° C, preferably at about 20° C, whereby such crystals extremely easy to be filtered off as those presented in the following Examples, are obtained.

Aqueous solutions containing fumaric acid in the ratios shown in the following table respectively are prepared according to the first and second steps of the present process. Two controls are prepared by using, in the second crystallization of fumaric acid, a cooling temperature higher than the upper limit shown in FIG. 2. In crystallizing the solutions and controls, the following specific filtration resistances are measured on the resulting malic acid crystals.

|  | Solutions of the present process | | | Controls | |
| --- | --- | --- | --- | --- | --- |
| Amount of fumaric acid (%) | 0.59 | 0.90 | 1.00 | 1.21 | 1.47 |
| Specific filtration resistance (m/kg) | $7.69 \times 10^7$ | $8.07 \times 10^7$ | $1.07 \times 10^8$ | $9.86 \times 10^8$ | $5.66 \times 10^9$ |

As apparent from the above data, in the cases of the solutions containing 1.0% or less of fumaric acid, the filtration of the crystals is carried out very easily. However, it is not accurate to conclude the ease in the filtration is attributed only to the low concentration of fumaric acid of 1.0% or less. The malic acid crystals obtained from these solutions have a very high purity and are therefore excellent as a food additive. When the second crystallization of fumaric acid is carried out at a temperature higher than the upper limit shown in FIG. 2, the filtrate obtained after removing the resulting crystals has a fumaric acid concentration of 1.0% or more. It is difficult to filter off the malic acid crystals precipitated in such a filtrate.

It is disadvantageous to carry out the second crystallization of fumaric acid at a temperature lower than the lower limit shown in FIG. 2, since a large amount of malic acid is crystallized together with fumaric acid.

In the following Reference Example, a conventional process for the production of malic acid is illustrated and in the other Examples the process of the present invention.

REFERENCE EXAMPLE

An aqueous 69.7% malic acid solution (70° C) containing fumaric acid in a ratio of 1.47% on the basis of the total amount of the acids, is prepared through a step of crystallization and separation of fumaric acid and a step of concentration as the first step. The aqueous solution is cooled to 20° C, whereby star-like crystals having a diameter of about 20 microns are obtained. The star-like crystal is an aggregate of cylindrical crystals of about 15 microns in length and about 3 microns in width. These crystals are difficult to be filtered off. The specific resistance of the crystals is $5.66 \times 10^9$ m/kg. The following is a result of the analysis of the crystal.
Malic acid — 78.35%
Fumaric acid — 3.77%
Maleic acid — 0.17%
Water — 17.71%

1.65 kg of the crystals is obtained from 6.45 kg of the feed solution used for the crystallization in the second step.

EXAMPLE 1

The aqueous 69.7% malic acid solution (70° C) containing fumaric acid in a ratio of 1.47% based on the total amount of the acids as mentioned in the foregoing Reference Example, is cooled to 50° C. After filtering off the resulting crystals, a filtrate containing fumaric acid in a ratio of 0.90% based on the total amount of the acids is obtained. (The above is the second step.)

The obtained filtrate is cooled to 20° C, whereby star-like crystals having a diameter of about 250 microns are obtained. The star-like crystal is an aggregate of cylindrical crystals of about 150 microns in length and about 60 microns in width. (The above is the third step.)

The filtration of these star-like crystals is very easy. The specific resistance of the crystals is $8.07 \times 10^7$ m/kg. The following is a result of the analysis of the crystal.
Malic acid — 93.30%
Fumaric acid — 1.69%
Maleic acid — 0.07%
Water — 4.97%

1.72 kg of the crystals is obtained from 8.38 kg of the feed solution used for the crystallization in the second step.

EXAMPLE 2

An aqueous 68.4% malic acid solution (65° C) containing fumaric acid in a ratio of 1.47% based on the total amount of the acids, is prepared through a step of crystallization and separation of fumaric acid and a step of decoloration and concentration as the first step. After filtering off the resulting crystals, a filtrate containing fumaric acid in a ratio of 0.59% based on the total amount of the acids is obtained. (The above is the second step.)

The obtained filtrate is cooled to 20° C, whereby star-like crystals having a diameter of about 200 microns are obtained. The star-like crystal is an aggregate of cylindrical crystals of about 120 microns in length and about 50 microns in width. (The above is the third step.)

The filtration of these star-like crystals is very easy. The specific resistance of the crystals is $7.69 \times 10^7$ m/kg. The following is a result of the analysis of the crystal.
Malic acid — 97.45%
Fumaric acid — 1.45%
Maleic acid — -
Water — 1.10%

1.33 kg of the crystals is obtained from 9.93 kg of the feed solution used for the crystallization in the second step.
What we claim is:
1. In the process for recovering crystals of malic acid from a reaction mixture obtained by reacting an aqueous solution of maleic acid or fumaric acid separately or together with heating, the improvement which comprises the steps of:

A. cooling the reaction mixture at a temperature of 10° to 40° C,
B. separating resulting solid matters from the mixture,
C. concentrating the resulting liquid,
D. cooling the concentrate having a concentration of 65–80% by weight at a temperature of about 20°–45° C at the lower weight percent and about 65°–75° C at the higher weight percent at a temperature in the shaded range in the attached FIG. 2,
E. separating resulting solid matters from the thus treated liquid and
F. separating crystallized malic acid from the resulting liquid at 19° to 21° C.

* * * * *